United States Patent [19]
Largent et al.

[11] Patent Number: 5,888,811
[45] Date of Patent: Mar. 30, 1999

[54] CORTICOTROPIN-RELEASING HORMONE RECEPTOR

[75] Inventors: Brian Lee Largent, Chadds Ford, Pa.; Ai-Ru Chen, Edison, N.J.; Walter Alan Kostich; Karen Marie Sperle, both of Hockessin, Del.

[73] Assignee: DuPont Pharmaceuticals Company, Wilmington, Del.

[21] Appl. No.: 861,249

[22] Filed: May 21, 1997

Related U.S. Application Data

[60] Provisional application No. 60/018,199, May 23, 1996.
[51] Int. Cl.$^6$ .......................... C07K 14/72; C12N 15/11; C12N 5/10; C12N 15/09
[52] U.S. Cl. .................... 435/320.1; 536/23.1; 536/23.5; 530/350; 530/300; 435/69.1; 435/252.3; 435/254.11; 435/325
[58] Field of Search .................................. 536/23.1, 23.5; 530/350, 300, 306; 435/320.1, 325, 252.3, 254.11, 69.1

[56] References Cited

FOREIGN PATENT DOCUMENTS

93/34651  12/1995  WIPO .

OTHER PUBLICATIONS

Liaw et al., Cloning and characterization of the human corticotropin–releasing factor–2 receptor complementary deoxyribonucleic acid, Encodrinology, 137(1): 72–77, Jan. 1996.

Perrin et al., Identification of a secon corticotropin–releasing factor receptor gene and characterization of a cDNA expressed in heart, Proc. Natl. Acad. Sci, USA, 92: 2969–2973, Mar. 1995.

Lerner, RA, Antibodies of predetermined specificity in biology and medicine, Adv. Immunol., 36: 1–43, 1984.

Stenzel et al., Identification of a novel murine receptor for corticotropin–releasing hormone expressed in the heart, Mol. Endocrinol., 9: 637–645, 1995.

*Primary Examiner*—Lila Feisee
*Assistant Examiner*—Claire M. Kaufman
*Attorney, Agent, or Firm*—Don M. Kerr; David H. Vance

[57] ABSTRACT

A novel human corticotropin releasing hormone (CRH) receptor which is a splice variant of the human $CRH_2$ receptor subfamily and is designated human CRHR2γ. Fragments of CRHR2γ. Nucleic acid molecules which encode CRHR2γ and fragments, expression vectors comprising the nucleic acid molecules, and host cells containing the expression vectors. Antibodies and antibody fragments capable of binding the novel receptor. Nucleic acid molecules capable of hybridizing with the above nucleic acid molecules. Use of the novel receptor and receptor fragments, antibodies and antibody fragments in testing compounds for CRH antagonist activity and in treating diseases.

24 Claims, No Drawings

CORTICOTROPIN-RELEASING HORMONE RECEPTOR

This applications claims priority to provisional application number 60/018,199, filed May 23,1996.

FIELD OF THE INVENTION

This invention relates to corticotropin-releasing hormone ("CRH") (also known as corticotropin-releasing factor, or CRF). More particularly, the invention relates to CRH receptors ("CRHR"), specifically subfamily 2 of CRH receptors ("$CRH_2$ receptors" or "CRHR2").

BACKGROUND OF THE INVENTION

CRH is a major neuropeptide mediator of the hypothalamic-pituitary-adrenocortical axis. It binds to plasma membrane receptors in the brain, pituitary, adrenals and spleen. It plays an important role in stress-responses and stress-induced disorders.

Neurocrine Biosciences, Inc. WO 95/34651, published Dec. 12, 1995, reports rat $CRF_{2\alpha}$ receptor ("rat CRFR2α"), rat $CRF_{2\beta}$ receptor ("rat CRFR2β"), and human $CRF_{2\alpha}$ receptor ("human CRFR2α"). Rat CRFR2α cDNA was isolated from a rat brain hypothalamus cDNA library. Rat CRFR2β cDNA was isolated from a rat brain cDNA library. Human CRFR2α receptor cDNA was isolated from a human brain cerebral cortex cDNA library. The cDNA molecules were sequenced, and the amino acid sequences of the receptor molecules were deduced from the cDNA sequences.

WO 95/34651 states that CRFR2α and CRFR2β can be cloned or synthesized and utilized to generate antibodies, which in turn can be utilized in flow cytometry to sort $CRF_2$ receptor-bearing cells, in histochemistry to stain $CRF_2$ receptor-bearing tissues, or in therapy to block binding of CRF to $CRF_2$ receptors. The application also states that the $CRF_2$ receptors can be used in various assays to identify compounds which bind the $CRF_2$ receptors, including agonists and antagonists.

SUMMARY OF THE INVENTION

We report here the cloning and characterization of a novel CRH receptor. Complementary DNA ("cDNA") was isolated from a human amygdala cDNA library and used to express a 397-amino acid protein with approximately 96% amino acid identity to the known human CRHR2α.

Sequence of the cDNA is shown in Sequence I.D. 1. Predicted sequence of the protein is shown in Sequence I.D. 2. The nucleotide sequence is identical to the nucleotide sequence for human CRHR2α (Sequence I.D. 3) from nucleotide 212 (Sequence I.D. 1). The predicted amino acid sequence is identical to the predicted amino acid sequence of human CRHR2α from amino acid 21. Thus the protein is a splice variant of the human $CRH_2$ receptor subfamily, and is designated "human CRH2γ receptor" or "human CRHR2γ".

As described below, the original CRHR2γ clone isolated from the human brain amygdala cDNA library contained a single codon deletion of three nucleotides (CAG), at 425–427 of Sequence I.D. 1. The deleted codon is present at a putative splice site in CRHR2γ and may reflect inaccuracy of splicing or alternative splicing choices at the splice junction for this individual cDNA clone. Both forms of CRHR2γ transcripts, those with and without the codon 425–427 of Sequence I.D. 1, have been detected at approximately equal levels by reverse transcriptase polymerase chain reaction amplification (RT-PCR) of mRNA from human brain.

Various cloning strategies have failed to identify the rat CRHR2γ homolog. Analysis of genomic DNA from humans and rats suggest the absence of this receptor gene in rat. While we have not excluded the possibility that CRHR2γ may be present in other species, at the moment it has only been found in humans and, thus, may be human specific.

Human CRHR2γ, when expressed in HEK293-EBNA cells, binds CRH, sauvagine and urotensin with the expected potency of stimulation of adenylate cyclase activity (sauvagine>urotensin>rat/human CRH ), as measured by intracellular cAMP accumulation. The CRH antagonist a-helical CRH (9–41) inhibits binding of the agonist peptide, CRH, and blocks the CRH-stimulated increase in intracellular cAMP. By RT-PCR analysis, the human $CRH_2\gamma$ receptor mRNA is present in human brain, in particular, amygdala, hippocampus, and has a distinct distribution of expression compared to the α and β isoforms of CRHR2. These differences in expression patterns may be significant for disease pathology and treatment.

This invention includes the following embodiments:

An isolated nucleic acid molecule encoding human CRHR2γ, including an isolated nucleic acid molecule comprising the sequence of nucleotides in Sequence I.D. No. 1 from nucleotide number 152 to nucleotide number 1342, and an isolated nucleic acid molecule comprising the same sequence but with deletion of the 425–427 CAG codon; also including an isolated nucleic acid molecule which encodes the sequence of amino acids in Sequence I.D. No. 2, and an isolated nucleic acid molecule which encodes the same sequence, but with deletion of the Gln residue at position 92.

An isolated nucleic acid molecule encoding the N-terminal extracellular domain of human CRHR2γ, including an isolated nucleic acid molecule comprising the sequence of nucleotides in Sequence I.D. No. 1, from nucleotide number 152 to nucleotide number 211, and also including an isolated nucleic acid molecule which encodes a protein having the sequence of amino acids in Sequence I.D. No. 2, from amino acid number 1 to amino acid number 20.

A recombinant expression vector comprising a promoter operably linked to any of the nucleic acid molecules described above, and a host cell containing such a recombinant expression vector.

An isolated human CRHR2γ, including an isolated human CRHR2γ with amino acid sequence of Sequence I.D. No. 2 and an isolated human CRHR2γ with the same sequence but with deletion of the Gin residue at position 92.

An isolated protein comprising the N-terminal extracellular domain of human CRHR2γ, including an isolated protein having the amino acid sequence of Sequence I.D. No. 2, from amino acid number 1 to amino acid number 20.

An isolated antibody or antibody fragment capable of specifically binding to a human CRHR2γ, especially an isolated antibody or fragment capable of specifically binding to the N-terminal extracellular domain of human CRHR2γ, including an isolated antibody or fragment capable of specifically binding to a protein having the amino acid sequence of Sequence I.D. No. 2, from amino acid number 1 to amino acid number 20.

An isolated nucleic acid molecule capable of specifically hybridizing with any of the nucleic acid molecules described above.

A method of testing a compound for pharmacological activity as a CRH antagonist which comprises adding the compound and a labeled CRH agonist such as $^{125}$I sauvagine to a sample containing human CRHR2γ or a fragment thereof, such as the N-terminal extracellular domain of human CRHR2γ, and measuring the extent to which the compound inhibits binding of the labeled agonist to the human CRHR2γ or fragment.

A method of treating a disease in a mammal which is associated with elevated levels of CRH or ACTH, comprising administering to the mammal a therapeutically effective amount of a human CRHR2γ or fragment thereof, such as the N-terminal extracellular domain of human CRHR2γ.

A method of treating a disease in a mammal which is associated with elevated levels of CRH or ACTH, comprising administering to the mammal a therapeutically effective amount of an antibody or antibody fragment capable of specifically binding to a human CRHR2γ or fragment thereof, such as the N-terminal extracellular domain of human CRHR2γ.

Diseases which are associated with elevated levels of CRH or ACTH include those mentioned in WO95/34651, i.e., Cushing's Disease, alcoholism, anorexia nervosa, pituitary tumors and other pituitary disorders, hypotension, immune system disorders such as arthritis, anxiety and depression.

DETAILED DESCRIPTION

The present invention relates to a novel CRHR2 protein. More particularly, the invention relates to an isolated nucleic acid encoding a novel splice isoform of the CRHR2 subfamily. This new subfamily member is designated CRHR2γ. Nucleic acids encoding CRHR2γ were identified in a human brain amygdala cDNA library using a DNA probe consisting of rat CRHR2 sequence obtained by polymerase chain reaction (PCR) amplification.

EXAMPLE 1

Cloning and sequencing of CRHR2γ cDNA A 536-bp polymerase chain reaction ("UPCR") fragment containing the nucleotides 1–536 of rat CRHR2α receptor cDNA (coding region) was used to screen a λgt11 human brain amygdala cDNA library (Clontech). The probe was labeled with [α-$^{32}$P]dCTP using a random primed labeling kit (Gibco-BRL). The plaques were lifted onto nitrocellulose membranes (Schleicher & Schuell), then denatured, neutralized and rinsed. The membranes were prehybridized at 60° C. in 6×SSC, 0.05×blotto (1×blotto: 5% non-fat dry milk, 0.02% sodium azide) and 100 µg/ml herring sperm DNA for 2 hours and then hybridized at the same condition with 1×10$^6$ cpm/ml labeled probe overnight. Membranes were washed with 2×SSC / 0.1% SDS consecutively at RT and 60° C. for 30 minutes each, then twice with 0.5×SSC / 0.1% SDS at 60° C. for 30 minutes. Approximately 8.5×10$^5$ phage plaques were screened and 5 unique hybridization-positive plaques were isolated and purified. λ phage DNA was isolated by Qiagen lambda kit and further characterized by Southern analysis. After subcloning CDNA inserts into pBluescript II SK (Stratagene), the DNA sequence of both strands was determined using automated fluorescent dideoxynucleotide chain termination methodology (Rosenthal, A. and Chamock-Jones, D. S.1993).

Of the five positive cDNA clones, one was homologous to the human CRHR1 (hCRHR1) subtype but revealed the inclusion of putative intronic sequence. Four of the cDNA clones represented genes of the human CRHR2 (hCRHR2) receptor subfamily. Two of these clones contained sequence that indicated a novel member of the hCRHR2 receptor subfamily which was an alternatively spliced form to the α or β hCRHR2 receptors. These clones included novel nucleotide sequence and predicted amino acid sequence in the presumptive extracellular portion of the receptor protein.

Human CRHR2γ contains a 1555-bp insert with a 1191-bp open reading frame encoding 397-a.a. protein (Sequence I.D. No. 1). Compared to known rat CRHR2α, this clone showed approximately 87% identity at the nucleotide level over the entire coding region and 90% identity at the amino acid level. When compared to the hCRHRI(Vita et al., 1993), hCRHR2γ is approximately 72% similar at the nucleotide and amino acid level. Identity between hCRHR2γ and hCRHR2α is more significant with 97% identity. According to the hydrophobicity analysis of hCRHR2γ amino acid sequence, it contains seven hydrophobic regions corresponding to seven putative transmembrane domains (TopPred II algorithm), and five potential N-linked glycosylation sites in the N terminus (Sequence I.D. No. 2). In all the species of cloned CRHR2 (Kishimoto et al., 1995; Lovenberg et aL, 1995; Perrin et al, 1995), all but one of the potential N-link glycosylation sites are preserved among them.

To obtain additional 5' sequence and validate the identity of the various alternatively spliced forms of the hCRHR2 gene, we used anchor PCR strategies to assess the sequence of the 5' end of messenger RNA containing sequence from the common region of the hCRHR2 subfamily. Three consecutive antisense oligonucleotide primers (SEQUENCE I.D. 4,5,6) were designed from the common sequence of hCRHR2, 3' from the putative splice site. After examining human brain hypothalamus, hippocampus and frontal cortex RNA by nested rounds of RT-PCR, we isolated an 5'RACE clone (from frontal cortex mRNA) with identical overlapping sequence to the hCRHR2γ clone and additional 5' non-coding sequence.

The original CRHR2γ clone isolated from the human brain amygdala cDNA library contained a single codon deletion of three nucleotides (CAG), at 425–427 of Sequence I.D. 1, compared to human homologs of CRHR α and β. The deleted three nucleotides (CAG) are present at a putative splice site in CRHR2γ and may reflect inaccuracy of splicing or an alternative splicing choice at the splice junction for this individual cDNA clone. The codon, CAG, which encodes for the amino acid glutamine, represents the consensus sequence at the 3' end of intronic sequence.

Both forms of CRHR2 gamma transcripts, those with and without the codon 425–427 of Sequence I.D. 1, have been detected at approximately equal levels by reverse transcriptase polymerase chain reaction amplification (RT-PCR) of mRNA from human brain. Thus, both transcript forms appear to be naturally transcribed, alternatively spliced forms of the CRHR2 gene.

Interestingly, unlike many other genes encoding G-protein-coupled receptors which lack introns in their coding sequence, the CRH receptor family appears to generate multiple isoforms by alternative RNA splicing. The mouse CRH receptor gene comprises at least 12 exons, spanning more than 14 Kb (Chen et. al ). Based on preliminary cloning and PCR analysis, we believe there might be more than two intron/exon spliced sites in hCRHR2 gene. Within the neuropeptide receptor family (Segre, G. R. and Goldring S. R.,1993), a rat growth hormone releasing hormone (GHRH) receptor gene has been reported that contains numerous introns within the coding region (Mayo, K E.,1992). The mRNA of porcine calcitonin receptor (CTR) gene also encompasses 14 exons with 12 exons encoding the protein (Zolnierowicz S. et al, 1994). The human glucagon receptor gene spans over 5.5 Kb and is interrupted by 12 introns (Lok S. et al., 1994) The type I human vasoactive intestinal peptide (VIP) receptor gene spans approximately 22 kb and is composed of 13 exons and 12 introns (Sreedharan S. P. et al., 1995). Extensive alternative splicing of mRNA represents a unique characteristic in this CRH/calcitonin/GHRH/glucagon/VIP family of G protein-coupled seven transmembrane domain receptors.

Tissue Distribution

To detect the human CRHR2γ message in various brain regions, we used the RT-PCR to examine the total and/or poly-A enriched RNA of human brain tissues. Specific oligonucleotide primers (Sequence I.D. 7,8) were used to PCR amplify CRHR2γ sequences. The resulting products were electrophoretically separated through an agarose gel and subsequently blotted to a nitrocellulose membrane for hybridization analysis with a $^{32}$P-labeled DNA probe for CRHR2γ. The signal for CRHR2γ was detected most abundantly in the human amygdala and hippocampus.

Heterologous Expression.

For expression studies, the full length CRHR2 γ cDNA (original cDNA library clone) was subcloned between the Xhol and Xbal restriction sites of expression vector phchm3AR (Shen et al., 1995), creating the CRHR2 γ expression plasmid ph-a10–18. This vector is a modification of pHEBo, an Epstein Barr Viral origin of replication plasmid (Sugden et al., 1985) into which a CMV immediate early promoter, a multicloning site, and the SV40 small t intron and early poly adenylation signal regions have been added. This plasmid replicates episomally in primate cells expressing the EBV nuclear antigen 1 (Shen et al., 1995).

A stable cell line expressing CRHR2 γ was established by transfecting the plasmid ph-a10–18 into HEK293EBNA cells (Invitrogen) using LipofectAMINE (GibcoBRL). This plasmid contains the CRHR2 γ gene under the control of the CMV immediate early promoter, the EBV oriP for maintenance of the plasmid as an extrachromosomal element in the appropriate cells (nonrodent mammalian cells expressing EBNA), and the hph gene from *E. coli* to yield resistance to hygromycin B. HEK293EBNA cells were grown in Dulbecco's modified Eagle medium containing 10% fetal bovine serum at 37° C. in a humid environment with 5% $CO_2$. Cells were plated at a density of $4 \times 10^5$ cells/well in a 6-well plate and transfected with 1 μg of plasmid per well the following day. Within 24 hours after transfection, the cells were expanded into 150 mm plates; within 24 hours after expansion, hygromycin B was added to the media at a concentration of 300 μg/ml to select for transfectants. All cells resistant to hygromycin B after a week must be harboring the plasmid within them; since no integration is necessary for the maintenance of the plasmid within these cells, all transfected cells are essentially the same and no further subcloning was necessary.

Receptor Binding Assays $^{125}$I-tyr-0-sauvagine was used in receptor binding studies with membranes isolated from HEK293EBNA cells expressing the CRHR2 γ receptor. Buffer consisted of 50 mM HEPES, 10 mM $MgCl_2$, 2 mM EGTA, and 1 μg/ml each of aprotinin, leupeptin, and pepstatin at a final pH of 7.0. Bacitracin at 0.15 mM and ovalbumin at 0.1% were added to the buffer on the day of use. Assays were performed at 23° C. for 4 hours in a final volume of 200 μl in 96-well microtiter plates. Reactions were initiated by the addition of 10–20 μg of membrane homogenates and terminated by rapid filtration through presoaked (0.3% polyethyleneimine) glass fiber filters using an Inotech 96-well harvester. The filters were washed quickly 3×with ice-cold solution (PBS+ 0.01% TritonX-100, pH7.2), dried briefly, then placed into polystyrene tubes and counted on an Isomedic 10/880 γ counter (counting efficiency ~80%). Data was analyzed by nonlinear regression analysis using the computer program MacLigand. Determinations were made from at least 3 separate experiments.

Saturation experiments were performed with 23 different concentrations of sauvagine over the range of 4 pM to 100 nM, using increasing concentrations of $^{125}$I-tyr-0-sauvagine from 4 pM to 1 nM, and 0.25 nM $^{125}$I-tyr-0-sauvagine spiked with unlabelled sauvagine from 1 nM to 100 nM. Nonspecific binding was defined by the presence of 1 μM a-helical CRH (9–41). The data analysis indicates the presence of two affinity states of the receptor: the high affinity receptor has a Kd of ~60 pM, and the low affinity one of ~5 nM. The Bmax of the high affinity receptor is ~100 fmole/mg protein and that of the low affinity receptor is ~1.6 pmole/mg protein.

Displacement studies looked at varying concentrations of r/h CRH, a-helical CRH(9–41), urotensin, and urocortin for their ability to displace 60–70 pM $^{125}$I-tyr-0-sauvagine. The approximate IC50s determined for these peptides are: r/h CRH 25 nM; a-helical CRH (9–41) 7 nM; urotensin 5 nM; urocortin 2 nM.

Whole Cell Adenylate Cyclase Assay:

HEK293EBNA cells expressing the CRHR2 γ were incubated in DMEM with low serum (0.1% FBS) at 37° C., 5% $CO_2$ for at least 2 hrs before the addition of isobytylmethoxyxanthine (IBMX) to the media at a final concentration of 0.1 mM. The cells were incubated with the IBMX for 30 minutes; test peptides or compounds were then added to the media and incubated therein for 25–30 min. The media was then aspirated from the cells and replaced with ice cold sodium acetate buffer containing 1 mM IBMX. The cells were then disrupted by a freeze-thaw, followed by sonication. Supernatants were assayed for cAMP levels with PerSeptive Diagnostics EIA Kit. Results indicate that respective $EC_{50}$ of r/h CRH>urotensin>sauvagine for cAMP stimulation at this receptor. The CRH receptor antagonist a-helical CRH (9–41) inhibits the stimulation of both r/h CRH and sauvagine.

Bibliography

Chalmers, D. T., Lovenberg, T. W., & De Souza, E. B. (1955). Localization of Novel Corticotropic-Releasing Factor Receptor ($CRF_2$) mRNA Expression to Specific Subcortical Nuclei in Rat Brain: Comparison with $CRF_1$ receptor mRNA Expression. *The Journal of Neuroscience*. 15(10), 6340–6350.

Chen, R., Lewis, K., Perrin, M. H., Vale, W. W. (1994), Characterization of the mouse CRF receptor gene. *The Endocrine Society Program and Abstracts*, 217.

De Souza, E. B., & Grigoriadis, D. E. (1995). *Physiology. Pharmacology. and role in Central Nervous System and Immune Disorders.* New York: Raven Press, Ltd.

Dohiman, H. G., Thomer, J., Caron, M. G., & Lefkowitz, R. J. (1991). Model systems for the study of seven-transmembrane segment receptors. *Annu. Rev. Blochem.*, 60, 653–88.

Kishimoto, T., Pearse, R. V., Lin, C. R., & Rosenfeld, M. G. (1995). A sauvagine/corticotropin-releasing factor receptor expressed in heart and skeletal muscle. *Proc. Natl. Acad. Sci. USA.* 92, 1108–1112.

Lok, S., Kuijper, J. L., Jelinek, L. J., Kramer, J. M., Whitmore, T. E., Sprecher, C. A., Mathewes, S., Grant, F. J., Biggs, S. H., Rosenberg, G. B., & al., e. (1994). The human glucagon receptor encoding gene: structure, cDNA sequence and chromosomal localization. *Gene.,* 150(2), 203–9.

Lovenberg, T. W. Chalmers, D. T., Liu, C., & De Souza, E. B. (1995). $CRF_{2a}$ and $CRF_{2b}$ receptor mRNAs are differently distributed beween the rat central nervous system and peripheral tissues. *Endocrinology.* 136 (9), 4139–4142.

Lovenberg, T. W., Liaw, C. W., grigoriadis, D. E., Clevenger, W., Chalmers, D. T., De Souza, E. B., & Oltersdorf, T. (1995). Cloning characterization of a functionally distinct corticotropin-releasing factor receptor subtype from rat brain. *Proc. Natl. Acad. Sci. USA.* 92, 836–8400.

Mayo, K. E. (1992). Molecular cloning and expression of a pituitary-specific receptor for growth hormone-releasing hormone. Molecular Endocrinology. 6(10), 1734–1744.

Owens, M. J., Vargas, M. A., Knight, D. L., & Nemeroff, C. B. (1991). The effects of alprazolam on corticotropin-releasing factor neurons in the rat brain: acute time course, chronic treatment and abrupt withdrawal. *J. Pharmacol. Exp. Ther.,* 258, 349–356.

Perrin, M. H., Donaldson, C. J., Chen, R., Lewis, K. A., & Vale, W. W. (1993). Cloning and functional expression of a rat brain corticotropin releasing factor (CRF) receptor. *Endocrinology.* 133, 3058–3061.

Perrin, M., Donaldson, C., Chen, R., Blount, A., Berggren, T., Bilezikjian, L., Sawchenko, P., & Vale, W. (1995). Identification of a second corticotropin-releasing factor receptor gene and characteriztion of a cDNA expressed in heart. *Proc. Natl. Acad. Sci. USA.* 92, 2969–2973.

Potter, E., Sutton, S., Donaldson, C., Chen, R., Perrin, M., Lewis, K., Sawchenko, P. E., & Vale, W. (1994). Distribution of corticotropin-releasing factor receptor expressin in the rat brain and pituitary. *Proc. Natl. Acad. Sci. USA.* 91, 8777–8781.

Rosenthal, A., & Chamock-Jones, D. S. (1993). Double-stranded DNA templates were sequenced with custom primers and using automated fluorescent Sanger dideoxy-nucleotide chain termination methodology. *Meth. Molec. Biol.,* 23, 281–296.

Sergre, G. V., & Goldring, S. R. (1993). Receptors for secretin, calcitonin, parathyroid hormone (PTH)/PTH-related peptide, vasoactive intestinal peptide, glucagon-like peptide 1, growth hormone-releasing hormone, and glucagon belong to a newly discovered g-protein-linked receptor family. *TEM.* 4(10), 309–314.

Shen, E. S., Cooke, G. M., & Horlick, R. A. (1985). Improved expression coning using receptor genes and Epstein-Barr virus ori-containing vectors. *Gene.* 156, 235–239.

Sreedgaran, S. P., Huang, J. X., Cheung, M. C., & Goetzl, E. J. (1995). Structure, expression, and chromosomal localization of the type I human vasoactive intestinal peptide receptor gene. *Proc. Natl. Acad. Sci. of the USA.* 92(7), 2939–43.

Stenzel, P., Kesterson, R. Yeung, W., Cone, R. D., Rittenberg, M. B., & Stenzel-Pooer, M. P. (1995). Identification of a novel murine receptor for corticotropin-releasing hormone expressed in the heart. *Molecular Endocrinology,* 637–645.

Sudgen, B., Marsh, K., & Yates, J. L. (1985). A vector that replicates as a plasmid and can be efficiently selected in B-lymphoblasts transformed by epstein barr virus. *Mol. Cell. Biol.,* 5, 410–413.

Vaughn, J., Donaldson, C., Bittencourt, J., Perrin, M. H., Lewis, K., Sutton, S., Chan, R., Tumbull, A. V., Lolvejoy, D., Rivier, C., Rivier, J., Sawchenko, P. E., & Vale, W. (1995). Urocortin, a mammalian neuropeptide related to fish urothnsin I and to corticotropin-releasing factor. *Nature.* 378(16), 287–292.

Vita, N., Laurent, P., Lefort, S., Chalon, P., Lelias, J. M., Kaghad, M., Le Fur, G., Caput, D., & Ferrara, P. (1993). Primary structure and functional expression of mouse pituitary and human brain corticotrophin releasing factor receptors. *FEBS,* 335(1), 1–5.

Wong, M. L., Licinio, J., Pasternak, K. I., & Gold, P. W. (1994). Localization of corticotropin-relasing hormone (CRF) receptor mRNA in adult rat brain in situ hybridization histochemistry. *Endocrinology.* 135(5), 2275–2278.

Zolnierowicz, S., Cron, P., Solinas-Toldo, S., Fries, R., Lin, H. Y., & Hemmings, B. A. (1994). Isolation, characterization, and chromosomal localization of the porcine calcitonin receptor gene. Identification of two variants of the receptor generated by alternative splicing. *Journal of Biological Chemistry.* 269(30), 19530–8.

---

SEQUENCE LISTING ( 1 ) GENERAL INFORMATION:

( i i i ) NUMBER OF SEQUENCES:8

( 2 ) INFORMATION FOR SEQ ID NO:1:

( i ) SEQUENCE CHARACTERISTICS:
        ( A ) LENGTH:1558 nucleotides
        ( B ) TYPE:nucleic acid
        ( C ) STRANDEDNESS:single
        ( D ) TOPOLOGY:linear ( i i ) FEATURE:
        ( A ) NAME/KEY:CDS
        ( B ) LOCATION:152...1342

( i i i ) SEQUENCE DESCRIPTION:SEQ ID NO:1:

-continued

| | | | | |
|---|---|---|---|---|
| CTGTGCTCAA | GCAATCTGCC | TACCTTGGCT | TCCCCAAGTG | CTGAGATTAT | 50 |
| GGGTGTGAGC | CACTGCACCT | GGCCAAGAAT | CCGAATGGAT | TCAAAGATAC | 100 |
| CTTGAAATAA | TTCCTCAATG | CAACACACAC | ACATATGCCA | GGGTTGGT | 148 |

```
CAA ATG GGA AGA GAG CCT TGG CCT GAA GAC AGG GAC CTG GGC                         190
    Met Gly Arg Glu Pro Trp Pro Glu Asp Arg Asp Leu Gly
     1               5                       10

TTT CCT CAG CTC TTC TGC CAA GGT CCC TAC TCC TAC TGC AAC                         232
Phe Pro Gln Leu Phe Cys Gln Gly Pro Tyr Ser Tyr Cys Asn
    15                  20                      25

ACG ACC TTG GAC CAG ATC GGA ACG TGC TGG CCC CGC AGC GCT                         274
Thr Thr Leu Asp Gln Ile Gly Thr Cys Trp Pro Arg Ser Ala
        30                  35                      40

GCC GGA GCC CTC GTG GAG AGG CCG TGC CCC GAG TAC TTC AAC                         316
Ala Gly Ala Leu Val Glu Arg Pro Cys Pro Glu Tyr Phe Asn
            45                  50                      55

GGC GTC AAG TAC AAC ACG ACC CGG AAT GCC TAT CGA GAA TGC                         358
Gly Val Lys Tyr Asn Thr Thr Arg Asn Ala Tyr Arg Glu Cys
                60                  65

TTG GAG AAT GGG ACG TGG GCC TCA AAG ATC AAC TAC TCA CAG                         400
Leu Glu Asn Gly Thr Trp Ala Ser Lys Ile Asn Tyr Ser Gln
70                  75                      80

TGT GAG CCC ATT TTG GAT GAC AAG CAG AGG AAG TAT GAC CTG                         442
Cys Glu Pro Ile Leu Asp Asp Lys Gln Arg Lys Tyr Asp Leu
    85                  90                      95

CAC TAC CGC ATC GCC CTT GTC GTC AAC TAC CTG GGC CAC TGC                         484
His Tyr Arg Ile Ala Leu Val Val Asn Tyr Leu Gly His Cys
        100                 105                     110

GTA TCT GTG GCA GCC CTG GTG GCC GCC TTC CTG CTT TTC CTG                         526
Val Ser Val Ala Ala Leu Val Ala Ala Phe Leu Leu Phe Leu
            115                 120                     125

GCC CTG CGG AGC ATT CGC TGT CTG CGG AAT GTG ATT CAC TGG                         568
Ala Leu Arg Ser Ile Arg Cys Leu Arg Asn Val Ile His Trp
                130                 135

ACC CTC ATC ACC ACC TTT ATC CTG CGA AAT GTC ATG TGG TTC                         610
Asn Leu Ile Thr Thr Phe Ile Leu Arg Asn Val Met Trp Phe
140                 145                     15

CTG CTG CAG CTC GTT GAC CAT GAA GTG CAC GAG AGC AAT GAG                         652
Leu Leu Gln Leu Val Asp His Glu Val His Glu Ser Asn Glu
    155                 160                     165

GTC TGG TGC CGC TGC ATC ACC ACC ATC TTC AAC TAC TTC GTG                         694
Val Trp Cys Arg Cys Ile Thr Thr Ile Phe Asn Tyr Phe Val
        170                 175                     180

GTG ACC AAC TTC TTC TGG ATG TTT GTG GAA GGC TGC TAC CTG                         736
Val Thr Asn Phe Phe Trp Met Phe Val Glu Gly Cys Tyr Leu
            185                 190                     195

CAC ACG GCC ATT GTC ATG ACC TAC TCC ACT GAG CGC CTG CGC                         778
His Thr Ala Ile Val Met Thr Tyr Ser Thr Glu Arg Leu Arg
                200                 205

AAG TGC CTC TTC CTC TTC ATC GGA TGG TGC ATC CCC TTC CCC                         820
Lys Cys Leu Phe Leu Phe Ile Gly Trp Cys Ile Pro Phe Pro
210                 215                     220

ATC ATC GTC GCC TGG GCC ATC GGC AAG CTC TAC TAT GAG AAT                         862
Ile Ile Val Ala Trp Ala Ile Gly Lys Leu Tyr Tyr Glu Asn
    225                 230                     235

GAA CAG TGC TGG TTT GGC AAG GAG CCT GGC GAC CTG GTG GAC                         904
Glu Gln Cys Trp Phe Gly Lys Glu Pro Gly Asp Leu Val Asp
        240                 245                     250

TAC ATC TAC CAA GGC CCC ATC ATT CTC GTG CTC CTG ATC AAT                         946
Tyr Ile Tyr Gln Gly Pro Ile Ile Leu Val Leu Leu Ile Asn
```

```
                              255                          260                               265
TTC  GTA  TTT  CTG  TTC  AAC  ATC  GTC  AGG  ATC  CTA  ATG  ACA  AAG           988
Phe  Val  Phe  Leu  Phe  Asn  Ile  Val  Arg  Ile  Leu  Met  Thr  Lys
                    270                      275

TTA  CGC  GCG  TCC  ACC  ACA  TCC  GAG  ACA  ATC  CAG  TAC  AGG  AAG          1030
Leu  Arg  Ala  Ser  Thr  Thr  Ser  Glu  Thr  Ile  Gln  Tyr  Arg  Lys
280                      285                            290

GCA  GTG  AAG  GCC  ACC  CTG  GTG  CTC  CTG  CCC  CTG  CTG  GGC  ATC          1072
Ala  Val  Lys  Ala  Thr  Leu  Val  Leu  Leu  Pro  Leu  Leu  Gly  Ile
          295                      300                       305

ACC  TAC  ATG  CTC  TTC  TTC  GTC  AAT  CCC  GGG  GAG  GAC  GAC  CTG          1114
Thr  Tyr  Met  Leu  Phe  Phe  Val  Asn  Pro  Gly  Glu  Asp  Asp  Leu
               310                      315                       320

TCA  CAG  ATC  ATG  TTC  ATC  TAT  TTC  AAC  TCC  TTC  CTG  CAG  TCG          1156
Ser  Gln  Ile  Met  Phe  Ile  Tyr  Phe  Asn  Ser  Phe  Leu  Gln  Ser
                    325                      330                       335

TTC  CAG  GGT  TTC  TTC  GTG  TCT  GTC  TTC  TAC  TGC  TTC  TTC  AAT          1198
Phe  Gln  Gly  Phe  Phe  Val  Ser  Val  Phe  Tyr  Cys  Phe  Phe  Asn
                         340                      345

GGA  GAG  GTG  CGC  TCA  GCC  GTG  AGG  AAG  AGG  TGG  CAC  CGC  TGG          1240
Gly  Glu  Val  Arg  Ser  Ala  Val  Arg  Lys  Arg  Trp  His  Arg  Trp
350                           355                      360

CAG  GAC  CAT  CAC  TCC  CTT  CGA  GTC  CCC  ATG  GCC  CGG  GCC  ATG          1282
Gln  Asp  His  His  Ser  Leu  Arg  Val  Pro  Met  Ala  Arg  Ala  Met
          365                           370                      375

TCC  ATC  CCT  ACA  TCA  CCC  ACA  CGG  ATC  AGC  TTC  CAC  AGC  ATC          1324
Ser  Ile  Pro  Thr  Ser  Pro  Thr  Arg  Ile  Ser  Phe  His  Ser  Ile
               380                           385                      390

AAG  CAG  ACG  GCC  GCT  GTG  TGA  CCCCTCGGTC  GCCCACCTGC  ACAGCTC            1372
Lys  Gln  Thr  Ala  Ala  Val
                    395

CCCTGTCCTC  CTCCACCTTC  TTCCTCTGGG  TTCTCTGTGC  TGGGCAGGCT                    1422

CTCGTGGGGC  AGGAGATGGG  AGGGGAGAGA  CCAGCTCTCC  AGCCTGGCAG                    1472

GAAAGAGGGG  GTGCGGCAGC  CAAGGGGGAC  TGCAAGGGAC  AGGGATGAGT                    1522

GGGGGCCACC  AGGCTCAGCG  CAAGAGGAAG  CAGAGG                                    1558
```

( 2 ) INFORMATION FOR SEQ ID NO:2:

( i ) SEQUENCE CHARACTERISTICS:
        ( A ) LENGTH:397 amino acids
        ( B ) TYPE:amino acid
        ( C ) TOPOLOGY:linear ( i i ) MOLECULE TYPE:protein ( i i i ) SEQUENCE DESCRIPTION:SEQ ID NO:2:

```
Met  Gly  Arg  Glu  Pro  Trp  Pro  Glu  Asp  Arg  Asp  Leu  Gly
1                   5                        10

Phe  Pro  Gln  Leu  Phe  Cys  Gln  Gly  Pro  Tyr  Ser  Tyr  Cys  Asn
     15                      20                      25

Thr  Thr  Leu  Asp  Gln  Ile  Gly  Thr  Cys  Trp  Pro  Arg  Ser  Ala
          30                           35                      40

Ala  Gly  Ala  Leu  Val  Glu  Arg  Pro  Cys  Pro  Glu  Tyr  Phe  Asn
               45                           50                      55

Gly  Val  Lys  Tyr  Asn  Thr  Thr  Arg  Asn  Ala  Tyr  Arg  Glu  Cys
                    60                           65

Leu  Glu  Asn  Gly  Thr  Trp  Ala  Ser  Lys  Ile  Asn  Tyr  Ser  Gln
70                        75                           80
```

| | | | | | | | | | | | |
|---|---|---|---|---|---|---|---|---|---|---|---|
| Cys | Glu | Pro | Ile | Leu | Asp | Asp | Lys | Gln | Arg | Lys | Tyr | Asp | Leu |
| 85 | | | | | 90 | | | | | 95 | |
| His | Tyr | Arg | Ile | Ala | Leu | Val | Val | Asn | Tyr | Leu | Gly | His | Cys |
| | | 100 | | | | 105 | | | | | 110 |
| Val | Ser | Val | Ala | Ala | Leu | Val | Ala | Ala | Phe | Leu | Leu | Phe | Leu |
| | | | 115 | | | | | 120 | | | | | 125 |
| Ala | Leu | Arg | Ser | Ile | Arg | Cys | Leu | Arg | Asn | Val | Ile | His | Trp |
| | | | | 130 | | | | | 135 |
| Asn | Leu | Ile | Thr | Thr | Phe | Ile | Leu | Arg | Asn | Val | Met | Trp | Phe |
| 140 | | | | | 145 | | | | | 150 |
| Leu | Leu | Gln | Leu | Val | Asp | His | Glu | Val | His | Glu | Ser | Asn | Glu |
| | 155 | | | | | 160 | | | | | 165 |
| Val | Trp | Cys | Arg | Cys | Ile | Thr | Thr | Ile | Phe | Asn | Tyr | Phe | Val |
| | | 170 | | | | | 175 | | | | | 180 |
| Val | Thr | Asn | Phe | Phe | Trp | Met | Phe | Val | Glu | Gly | Cys | Tyr | Leu |
| | | | 185 | | | | | 190 | | | | | 195 |
| His | Thr | Ala | Ile | Val | Met | Thr | Tyr | Ser | Thr | Glu | Arg | Leu | Arg |
| | | | | 200 | | | | | 205 |
| Lys | Cys | Leu | Phe | Leu | Phe | Ile | Gly | Trp | Cys | Ile | Pro | Phe | Pro |
| 210 | | | | | 215 | | | | | 220 |
| Ile | Ile | Val | Ala | Trp | Ala | Ile | Gly | Lys | Leu | Tyr | Tyr | Glu | Asn |
| | 225 | | | | | 230 | | | | | 235 |
| Glu | Gln | Cys | Trp | Phe | Gly | Lys | Glu | Pro | Gly | Asp | Leu | Val | Asp |
| | | 240 | | | | | 245 | | | | | 250 |
| Tyr | Ile | Tyr | Gln | Gly | Pro | Ile | Ile | Leu | Val | Leu | Leu | Ile | Asn |
| | | | 255 | | | | | 260 | | | | | 265 |
| Phe | Val | Phe | Leu | Phe | Asn | Ile | Val | Arg | Ile | Leu | Met | Thr | Lys |
| | | | | 270 | | | | | 275 |
| Leu | Arg | Ala | Ser | Thr | Thr | Ser | Glu | Thr | Ile | Gln | Tyr | Arg | Lys |
| 280 | | | | | 285 | | | | | 290 |
| Ala | Val | Lys | Ala | Thr | Leu | Val | Leu | Leu | Pro | Leu | Leu | Gly | Ile |
| | 295 | | | | | 300 | | | | | 305 |
| Thr | Tyr | Met | Leu | Phe | Phe | Val | Asn | Pro | Gly | Glu | Asp | Asp | Leu |
| | | 310 | | | | | 315 | | | | | 320 |
| Ser | Gln | Ile | Met | Phe | Ile | Tyr | Phe | Asn | Ser | Phe | Leu | Gln | Ser |
| | | | 325 | | | | | 330 | | | | | 335 |
| Phe | Gln | Gly | Phe | Phe | Val | Ser | Val | Phe | Tyr | Cys | Phe | Phe | Asn |
| | | | | 340 | | | | | 345 |
| Gly | Glu | Val | Arg | Ser | Ala | Val | Arg | Lys | Arg | Trp | His | Arg | Trp |
| 350 | | | | | 355 | | | | | 360 |
| Gln | Asp | His | His | Ser | Leu | Arg | Val | Pro | Met | Ala | Arg | Ala | Met |
| | 365 | | | | | 370 | | | | | 375 |
| Ser | Ile | Pro | Thr | Ser | Pro | Thr | Arg | Ile | Ser | Phe | His | Ser | Ile |
| | | 380 | | | | | 385 | | | | | 390 |
| Lys | Gln | Thr | Ala | Ala | Val |
| | | | 395 |

( 2 ) INFORMATION FOR SEQ ID NO:3:

( i ) SEQUENCE CHARACTERISTICS:
        ( A ) LENGTH:1233 nucleotides
        ( B ) TYPE:nucleic acid
        ( C ) STRANDEDNESS:single
        ( D ) TOPOLOGY:linear ( i i i ) SEQUENCE DESCRIPTION:SEQ ID NO:3:

```
ATGGACGCGG  CACTGCTCCA  CAGCCTGCTG  GAGGCCAACT  GCAGCCTGGC           50
GCTGGCTGAA  GAGCTGCTCT  TGGACGGCTG  GGGGCCACCC  CTGGACCCCG          100
AGGGTCCCTA  CTCCTACTGC  AACACGACCT  TGGACCAGAT  CGGAACGTGC          150
TGGCCCCGCA  GCGCTGCCGG  AGCCCTCGTG  GAGAGGCCGT  GCCCCGAGTA          200
CTTCAACGGC  GTCAAGTACA  ACACGACCCG  GAATGCCTAT  CGAGAATGCT          250
TGGAGAATGG  GACGTGGGCC  TCAAAGATCA  ACTACTCACA  GTGTGAGCCC          300
ATTTTGGATG  ACAAGCAGAG  GAAGTATGAC  CTGCACTACC  GCATCGCCCT          350
TGTCGTCAAC  TACCTGGGCC  ACTGCGTATC  TGTGGCAGCC  CTGGTGGCCG          400
CCTTCCTGCT  TTTCCTGGCC  CTGCGGAGCA  TTCGCTGTCT  GCGGAATGTG          450
ATTCACTGGA  ACCTCATCAC  CACCTTTATC  CTGCGAAATG  TCATGTGGTT          500
CCTGCTGCAG  CTCGTTGACC  ATGAAGTGCA  CGAGAGCAAT  GAGGTCTGGT          550
GCCGCTGCAT  CACCACCATC  TTCAACTACT  TCGTGGTGAC  CAACTTCTTC          600
TGGATGTTTG  TGGAAGGCTG  CTACCTGCAC  ACGGCCATTG  TCATGACCTA          650
CTCCACTGAG  CGCCTGCGCA  AGTGCCTCTT  CCTCTTCATC  GGATGGTGCA          700
TCCCCTTCCC  CATCATCGTC  GCCTGGGCCA  TCGGCAAGCT  CTACTATGAG          750
AATGAACAGT  GCTGGTTTGG  CAAGGAGCCT  GGCGACCTGG  TGGACTACAT          800
CTACCAAGGC  CCCATCATTC  TCGTGCTCCT  GATCAATTTC  GTATTTCTGT          850
TCAACATCGT  CAGGATCCTA  ATGACAAAGT  TACGCGCGTC  CACCACATCC          900
GAGACAATCC  AGTACAGGAA  GGCAGTGAAG  GCCACCCTGG  TGCTCCTGCC          950
CCTCCTGGGC  ATCACCTACA  TGCTCTTCTT  CGTCAATCCC  GGGGAGGACG         1000
ACCTGTCACA  GATCATGTTC  ATCTATTTCA  ACTCCTTCCT  GCAGTCGTTC         1050
CAGGGTTTCT  TCGTGTCTGT  CTTCTACTGC  TTCTTCAATG  GAGAGGTGCG         1100
CTCAGCCGTG  AGGAAGAGGT  GGCACCGCTG  GCAGGACCAT  CACTCCCTTC         1150
GAGTCCCCAT  GGCCCGGGCC  ATGTCCATCC  CTACATCACC  CACACGGATC         1200
GCTTCCACA   GCATCAAGCA  GACGGCCGCT  GTG                            1233
```

( 2 ) INFORMATION FOR SEQ ID NO:4:

( i ) SEQUENCE CHARACTERISTICS:
        ( A ) LENGTH:22 nucleotides
        ( B ) TYPE:nucleic acid
        ( C ) STRANDEDNESS:single
        ( D ) TOPOLOGY:linear ( i i i ) SEQUENCE DESCRIPTION:SEQ ID NO:4:

```
GGT CAT ACT TCC TCT GCT TGT C                                        22
```

( 2 ) INFORMATION FOR SEQ ID NO:5:

( i ) SEQUENCE CHARACTERISTICS:
        ( A ) LENGTH:20 nucleotides
        ( B ) TYPE:nucleic acid
        ( C ) STRANDEDNESS:single
        ( D ) TOPOLOGY:linear ( i i i ) SEQUENCE DESCRIPTION:SEQ ID NO:5:

```
TCT CCA AGC ATT CTC GAT AG                                           20
```

( 2 ) INFORMATION FOR SEQ ID NO:6:

( i ) SEQUENCE CHARACTERISTICS:

( A ) LENGTH:18 nucleotides
            ( B ) TYPE:nucleic acid
            ( C ) STRANDEDNESS:single
            ( D ) TOPOLOGY:linear ( i i i ) SEQUENCE DESCRIPTION:SEQ ID NO:6:

TAC TTG ACG CCG TTG AAG                                                                          1 8

( 2 ) INFORMATION FOR SEQ ID NO:7:

( i ) SEQUENCE CHARACTERISTICS:
            ( A ) LENGTH:20 nucleotides
            ( B ) TYPE:nucleic acid
            ( C ) STRANDEDNESS:single
            ( D ) TOPOLOGY:linear ( i i i ) SEQUENCE DESCRIPTION:SEQ ID NO:7:

TCT CCA AGC ATT CTC GAT AG                                                                       2 0

( 2 ) INFORMATION FOR SEQ ID NO:8:

( i ) SEQUENCE CHARACTERISTICS:
            ( A ) LENGTH:19 nucleotides
            ( B ) TYPE:nucleic acid
            ( C ) STRANDEDNESS:single
            ( D ) TOPOLOGY:linear ( i i i ) SEQUENCE DESCRIPTION:SEQ ID NO:8:

GAT TAT GGG TGT GAG CCA C                                                                        1 9

What is claimed as new and desired to be secured by Letter Patent of United States is:

1. An isolated nucleic acid molecule encoding human CRHR2γ or a fragment thereof, wherein the molecule or fragment encodes a protein comprising the sequence of amino acids in Sequence I.D. No. 2, from amino acid number 1 to amino acid number 20, and the human CRHR2γ binds to CRH (corticotropin-releasing factor), sauvagine and urotensin.

2. An isolated nucleic acid molecule of claim 1 which encodes a protein comprising the sequence of amino acids in Sequence I.D. No. 2.

3. An isolated nucleic acid molecule of claim 1 which encodes a protein comprising the sequence of amino acids in Sequence I.D. No. 2 with deletion of the Gln residue at position 92.

4. An isolated nucleic acid molecule encoding human CRHR2γ or a fragment thereof, wherein the molecule or fragment thereof comprises the sequence of nucleotides in Sequence I.D. No. 1, from nucleotide number 152 to nucleotide number 211 and the human CRHR2γ binds to CRH, sauvagine and urotensin.

5. An isolated nucleic acid molecule of claim 4 comprising the sequence of nucleotides in Sequence I.D. No. 1, from nucleotide number 152 to nucleotide number 1342.

6. An isolated nucleic acid molecule of claim 4 comprising the sequence of nucleotides in Sequence I.D. No. 1, from nucleotide number 152 to nucleotide number 1342 with deletion of the 425–427 CAG codon.

7. A recombinant expression vector comprising a promoter operably linked to a nucleic acid molecule encoding human CRHR2γ or a fragment thereof, wherein the molecule or fragment encodes a protein comprising the sequence of amino acids in Sequence I.D. No. 2, from amino acid number 1 to amino acid number 20, and the human CRHR2γ binds to CRH, sauvagine and urotensin.

8. A recombinant expression vector of claim 7, wherein the molecule or fragment encodes a protein comprising the sequence of amino acids in Sequence I.D. No. 2.

9. A recombinant expression vector of claim 7, wherein the molecule or fragment encodes a protein comprising the sequence of amino acids in Sequence I.D. No. 2 with the exception that the Gln residue at position 92 is deleted.

10. A host cell comprising a recombinant expression vector of claim 7.

11. A host cell comprising a recombinant expression vector of claim 8.

12. A host cell comprising a recombinant expression vector of claim 9.

13. A recombinant expression vector comprising a promoter operably linked to a nucleic acid molecule encoding human CRHR2γ or a fragment thereof, wherein the molecule or fragment thereof comprises the sequence of nucleotides in Sequence I.D. No. 1, from nucleotide number 152 to nucleotide number 211 and the human CRHR2γ binds to CRH, sauvagine and urotensin.

14. A recombinant expression vector of claim 13, wherein the nucleic acid molecule comprises the sequence of nucleotides in Sequence I.D. No. 1, from nucleotide number 152 to nucleotide number 1342.

15. A recombinant expression vector of claim 13, wherein the nucleic acid molecule comprises the sequence of nucleotides in Sequence I.D. No. 1, from nucleotide number 152 to nucleotide number 1342 with deletion of the 425–427 CAG codon.

16. A host cell comprising a recombinant expression vector of claim 13.

17. A host cell comprising a recombinant expression vector of claim 14.

18. A host cell comprising a recombinant expression vector of claim 15.

19. Recombinantly produced human CRHR2γ or fragment thereof, produced by the method of growing the host cell of claim 16 under conditions suitable for expression of the human CRHR2γ or fragment thereof, wherein the CRHR2γ or fragment thereof comprises the sequence of amino acids in Sequence I.D. No. 2, from amino acid number 1 to amino acid number 20, and the human CRHR2γ binds to CRH, sauvagine and urotensin.

20. Recombinantly produced human CRHR2γ of claim 19, wherein the human CRHR2γ comprises the sequence of amino acids in Sequence I.D. No. 2.

21. Recombinantly produced human CRHR2γ of claim 19, wherein wherein the human CRHR2γ comprises the sequence of amino acids in Sequence I.D. No. 2 with the exception that the Gln residue at position 92 is deleted.

22. An isolated human CRHR2γ protein or a fragment thereof, wherein the human CRHR2γ or fragment thereof comprises the sequence of amino acids in Sequence I.D. No. 2, from amino acid number 1 to amino acid number 20, and the human CRHR2γ binds to CRH, sauvagine and urotensin.

23. An isolated human CRHR2γ of claim 22, wherein the human CRHR2γ comprises the sequence of amino acids in Sequence I.D. No. 2.

24. An isolated human CRHR2γ of claim 22, wherein the human CRHR2γ comprises the sequence of amino acids in Sequence I.D. No. 2 with the exception that the Gln residue at position 92 is deleted.

* * * * *